US008271297B2

(12) United States Patent
Crooks et al.

(10) Patent No.: US 8,271,297 B2
(45) Date of Patent: *Sep. 18, 2012

(54) AUTOMATED ORDER ENTRY SYSTEM AND METHOD

(75) Inventors: Steven S. Crooks, Gladstone, MO (US); Christopher S. Finn, Liberty, MO (US); David P. McCallie, Jr., Stilwell, KS (US)

(73) Assignee: Cerner Innovation, Inc., Overland Park, KS (US)

( * ) Notice: Subject to any disclaimer, the term of this patent is extended or adjusted under 35 U.S.C. 154(b) by 128 days.

This patent is subject to a terminal disclaimer.

(21) Appl. No.: 12/981,009

(22) Filed: Dec. 29, 2010

(65) Prior Publication Data

US 2011/0099029 A1    Apr. 28, 2011

Related U.S. Application Data

(62) Division of application No. 10/679,567, filed on Oct. 6, 2003, now Pat. No. 7,970,621.

(60) Provisional application No. 60/419,577, filed on Oct. 18, 2002.

(51) Int. Cl.
    *G06Q 50/00*    (2006.01)
    *G06F 7/00*    (2006.01)
    *G06F 17/30*    (2006.01)

(52) U.S. Cl. ............... 705/2; 705/3; 707/706; 707/759; 707/780

(58) Field of Classification Search ........... 707/600, 707/759, 706; 705/2, 3
See application file for complete search history.

(56) References Cited

U.S. PATENT DOCUMENTS

| 6,202,062 | B1 * | 3/2001 | Cameron et al. ............ 1/1 |
| 6,377,945 | B1 * | 4/2002 | Risvik .................... 1/1 |

(Continued)

FOREIGN PATENT DOCUMENTS

DE    10358385 A1 *  7/2005

OTHER PUBLICATIONS

Lovis et al, "Evaluation of a Command-Line Parser-based Order Entry Pathway for the Department of Veterans Affairs Electronic Patient Record," Journal of the American Medical Informatics Association, vol. 8, No. 5, Sep./Oct. 2001, pp. 486-496.*

(Continued)

*Primary Examiner* — Luke Gilligan
*Assistant Examiner* — Anita Molina
(74) *Attorney, Agent, or Firm* — Shook, Hardy & Bacon L.L.P.

(57) ABSTRACT

A computer-implemented method for facilitating placement of health care order entry is provided. The method includes receiving input indicative of a desired healthcare order. The order has certain terms therein that are normalized. The method also finds possible order matches for the normalized terms, and calculates a rough score for the possible order matches. The method refines the rough score with a rough score adjustment, and then ranks the found possible order matches from the most-likely to match the desired order to the least-likely based upon the refined rough score. These possible order matches can then be displayed to the user for selection.

6 Claims, 4 Drawing Sheets

U.S. PATENT DOCUMENTS

| | | | | |
|---|---|---|---|---|
| 6,542,902 | B2* | 4/2003 | Dulong et al. | 1/1 |
| 6,694,334 | B2* | 2/2004 | DuLong et al. | 604/189 |
| 6,934,767 | B1* | 8/2005 | Jellinek | 709/247 |
| 7,155,427 | B1* | 12/2006 | Prothia et al. | 707/694 |
| 7,287,002 | B1* | 10/2007 | Asher et al. | 705/26.8 |
| 7,624,029 | B1* | 11/2009 | Ghouri | 705/3 |
| 2002/0128816 | A1* | 9/2002 | Haug et al. | 704/4 |
| 2002/0165853 | A1* | 11/2002 | Gogolak | 707/3 |
| 2003/0014399 | A1* | 1/2003 | Hansen et al. | 707/3 |
| 2003/0069880 | A1* | 4/2003 | Harrison et al. | 707/3 |
| 2005/0262121 | A1* | 11/2005 | Cesare et al. | 707/100 |

OTHER PUBLICATIONS

Lovis, C. and Payne, T. "Extending the VA CPRS Electronic Patient Record Order Entry System Using Natural Language Processing Techniques." Proc AMIA Symp. 2000: 517-521.*

Teich, J. et al. "Response to a Trial of Physician-Based Inpatient Order Entry." Proc AMIA Symp. 1994: 316-320.*

Nelson, S. et al. "A Semantic Normal Form for Clinical Drugs in the UMLS: Early Experiences with the VANDF." Proc AMIA Symp. 2002: 557-561.*

* cited by examiner

AUTOMATED ORDER ENTRY SYSTEM AND METHOD

CROSS-REFERENCE TO RELATED APPLICATIONS

This application claims the benefit of U.S. Provisional Application Ser. No. 60/419,577, filed Oct. 18, 2002, and is a divisional application of U.S. Utility application Ser. No. 10/679,567, filed Oct. 6, 2003 both of which are hereby incorporated in their entirety by reference.

STATEMENT REGARDING FEDERALLY SPONSORED RESEARCH OR DEVELOPMENT

Not Applicable.

TECHNICAL FIELD

The present invention relates to a computer system and, more particularly, to a computer system for providing automated order entry in a medical environment.

BACKGROUND OF THE INVENTION

In the health care environment, physicians create orders in providing overall patient care. The order may specify a drug, along with its dosage and frequency. Typically, the doctor will hand write this order on a piece of paper. Alternatively, the physician may orally tell a nurse what to order, and the nurse will create the handwritten order. Handwritten orders must then be processed to administer the care required by the order. A risk is thus introduced that the handwritten order will not be legible, or that the handwritten order may not be complete in some respect. If the physician orally informs a nurse regarding the order, an additional risk of error is introduced in the transcription of the order by the nurse.

It would be desirable to allow the physician to place the order utilizing a computer keyboard, via a voice recognition device or other automated system. But an automated system must meet several requirements to be useful and effective. First, the automated system must take into account the time pressures associated with the provision of health care services. The system must be very user friendly, keeping in mind that the typical user will be a physician. The automated system should minimize the effort needed by the physician in the use of the system. Second, the automated system should be fast and easy to use. The physician should not be required to wait while extensive computer processing occurs. Third, the automated system should present the physician with a sorted or ranked set of options that most likely match the physician's intended order. These options should be sorted or ranked according to the most likely match for the order. Finally, the orders presented must be accurate.

BRIEF SUMMARY OF THE INVENTION

Generally described, a method in a computer system for the automated selection of a command line order is provided. The method includes receiving order input, normalizing the input, calculating a rough score, and then adjusting the rough score. Following the adjusting stage, the top or best matches are presented to the physician for final selection.

Additional advantages and novel features of the invention will be set forth in part in a description which follows, and in part will become apparent to those skilled in the art upon examination of the following, or may be learned by practice of the invention.

BRIEF DESCRIPTION OF THE SEVERAL VIEWS OF THE DRAWING

The present invention is described in detail below with reference to the attached drawing figures, wherein.

DETAILED DESCRIPTION OF THE INVENTION

Figure 5:
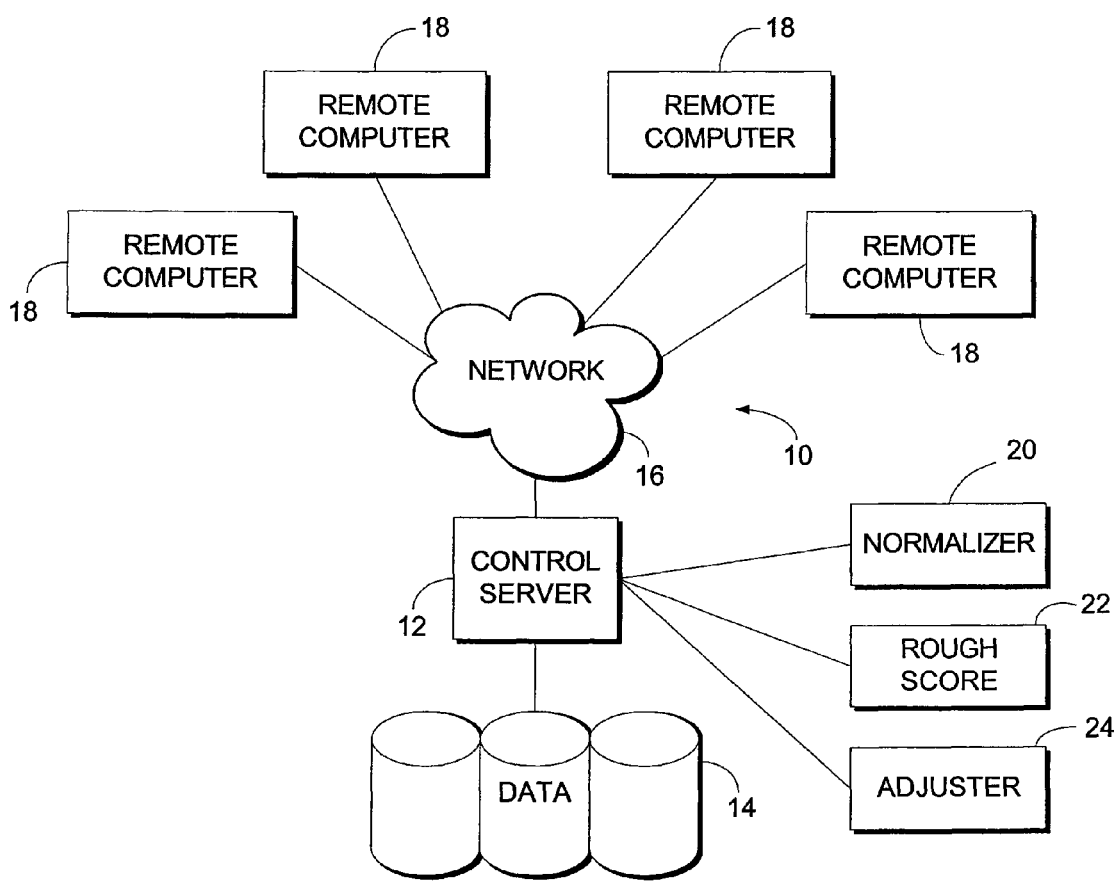
FIG. 5 is a schematic diagram of a suitable computing system environment for use in implementing the present invention.

The present invention provides a method and system for facilitating placement of healthcare orders. FIG. 5 illustrates an example of a suitable order entry computing system environment 10 on which the invention may be implemented. The order entry computing system environment 10 is only one example of a suitable computing environment and is not intended to suggest any limitation as to the scope of use or functionality of the invention. Neither should the computing environment 10 be interpreted as having any dependency or requirement relating to any one or combination of components illustrated in the exemplary environment 10.

The invention is operational with numerous other general purpose or special purpose computing system environments or configurations. Examples of well-known computing systems, environments, and/or configurations that may be suitable for use with the invention include, but are not limited to, personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, and the like.

The invention may be described in the general context of computer-executable instructions, such as program modules, being executed by a computer. Generally, program modules include, but are not limited to, routines, programs, objects, components, and data structures that perform particular tasks or implement particular abstract data types. The invention may also be practiced in distributed computing environments where tasks are performed by remote processing devices that are linked through a communications network. In a distributed computing environment, program modules may be located in both local and remote computer storage media, including memory storage devices.

With reference to FIG. 5, an exemplary order entry system for implementing the invention includes a general purpose computing device in the form of server 12. Components of server 12 may include, but are not limited to, a processing unit, internal system memory, and a suitable system bus for coupling various system components, including a database cluster 14 to the control server 12. The system bus may be any of several types of bus structures, including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

Server 12 typically includes therein or has access to a variety of computer readable media, for instance, database cluster 14. Computer readable media can be any available media that can be accessed by server 12, and includes both volatile and nonvolatile media, removable and nonremovable media. By way of example, and not limitation, computer readable media may comprise computer storage media and communication media. Computer storage media may be implemented in any method or technology for storage of information, such as computer readable instructions, data structures, program modules or other data. Computer storage media includes, but is not limited to, RAM, ROM, EEPROM, flash memory or other memory technology, CD-ROM, digital versatile disks (DVD), or other optical disk storage, magnetic cassettes, magnetic tape, magnetic disk storage, or other magnetic storage devices, or any other medium which can be used to store the desired information and which can be accessed by server 12. Communication media typically embodies computer readable instructions, data structures, program modules, or other data in a modulated data signal, such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media, such as a wired network or direct-wired connection, and wireless media such as acoustic, RF, infrared and other wireless media. Combinations of any of the above should also be included within the scope of computer readable media.

The computer storage media, including database cluster 14, discussed above and illustrated in FIG. 5, provide storage of computer readable instructions, data structures, program modules, and other data for server 12. Server 12 may operate in a computer network 16 using logical connections to one or more remote computers 18. Remote computers 18 can be located at a variety of locations in a medical environment, for example, but not limited to, hospitals, other inpatient settings, testing labs, medical billing and financial offices, and hospital administration. The remote computers may also be physically located in a non-traditional medical care environments so that the entire health care community is capable of integration on the network. Each remote computer 18 may be a personal computer, server, router, a network PC, an interfaced instrument, a peer device or other common network node, and may include some or all of the elements described above relative to server 12. Computer network 16 may be a local area network (LAN) and/or a wide area network (WAN), but may also include other networks. Such networking environments are commonplace in offices, enterprise-wide computer networks, intranets and the Internet. When utilized in a WAN networking environment, server 12 may include a modem or other means for establishing communications over the WAN, such as the Internet. In a networked environment, program modules or portions thereof may be stored in server 12, or database cluster 14, or on any of the remote computers 18. For example, and not limitation, various application programs may reside on the memory associated with any one or all of remote computers 18. It will be appreciated that the network connections shown are exemplary and other means of establishing a communications link between the computers may be used.

By way of example, a user may enter commands and information into server 12 or convey commands and information to the server 12 via remote computers 18 through input devices, such as keyboards or pointing devices, commonly referred to as a mouse, trackball, or touch pad. Other input devices may include accepting data from an interface or logic system, microphone, satellite dish, scanner or the like. Server 12 and/or remote computers 18 may have any sort of display device, for instance, a monitor. In addition to a monitor, server 12 and/or computers 18 may also include other peripheral output devices, such as speakers and printers.

Although many other internal components of server 12 and computers 18 are not shown, those of ordinary skill in the art will appreciate that such components and their interconnection are well known. Accordingly, additional details concerning the internal construction of server 12 and computers 18 need not be disclosed in connection with the present invention.

Figure 1:
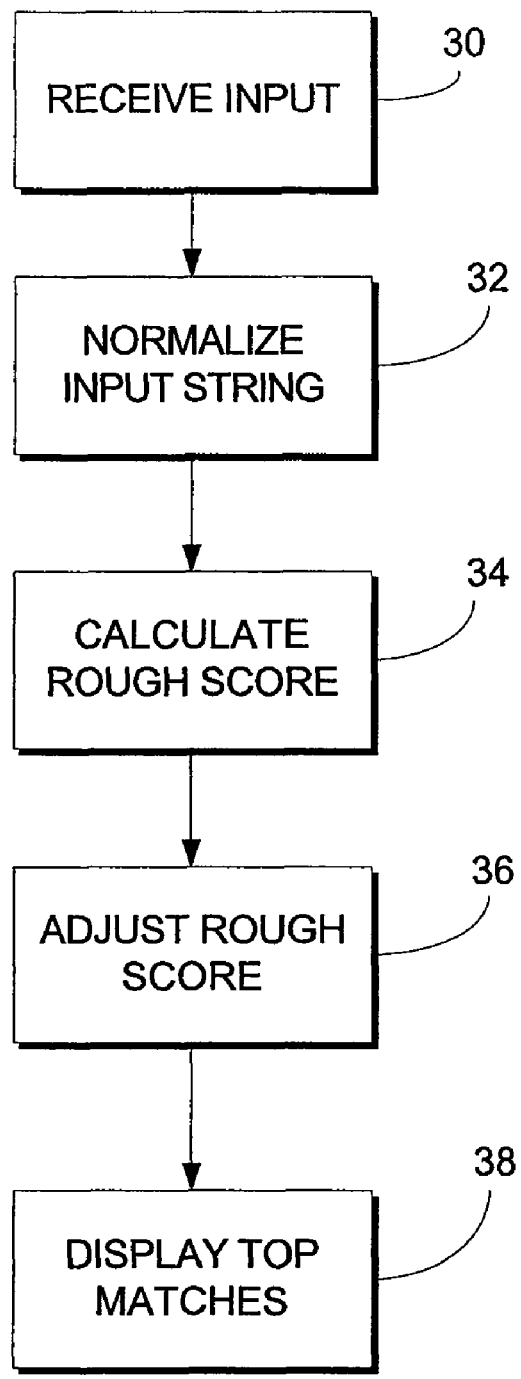
FIG. 1 is a flow diagram illustrating the overall method for the automated order entry.

As best seen in FIG. 1, the overall method for the automated command line order entry is illustrated. The process begins by receiving input from a user as shown at step 30. This input is received from one of the remote computers 18 via the network 16. The input received is normalized at step 32. After normalizing the input string, a rough score is calculated for matches or possible matches from the database. Once a rough score is calculated at step 34, the score is adjusted or finetuned at step 36. After the score has been fine-tuned for the possible matches, the top matches are displayed as shown at step 38. From an overall point of view, the system receives an input string from a user and returns to the user the best possible matches for user selection. Thereafter, the user can confirm which of the top matches was intended for the order. Each of the steps 32-36 are described more particularly with reference to FIGS. 2-4.

Figure 2:
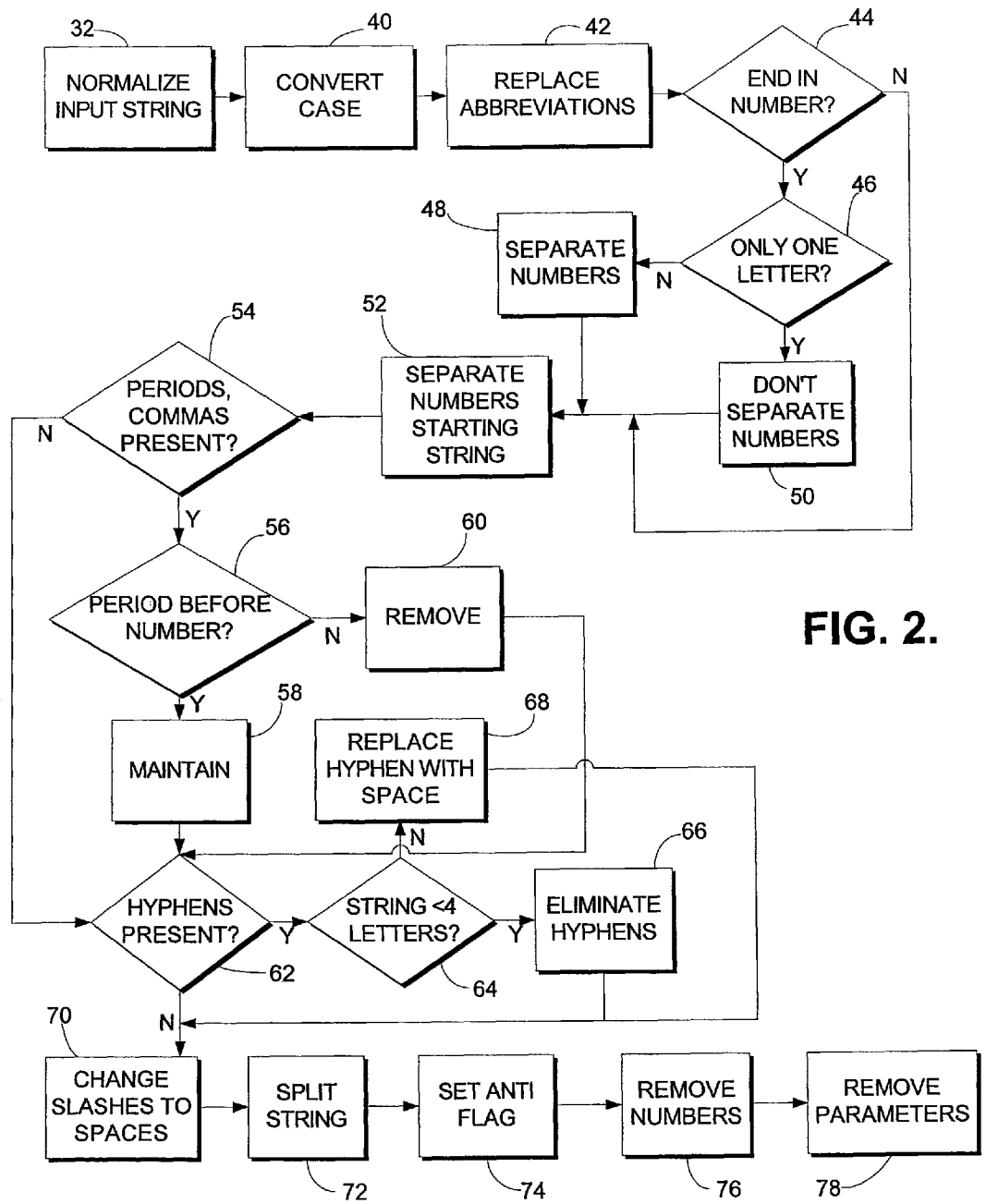
FIG. 2 is a flow diagram illustrating one portion of the overall method.

Turning to FIG. 2, the process of normalizing the input string is shown in flow diagram form. After the input string is received, the first step constructed by the normalizer 20 (FIG. 5) is to confirm the case of the terms in the input string, as shown at step 40. The case of the search terms is converted to match that existing in the database 14 (FIG. 5). It should be understood that all of the data within database 14 are pre-normalized in the same manner as the input strings as described with respect to FIG. 2. In a preferred embodiment, all the data in the database are converted to lower case. Thus, in step 40, all search terms are converted to lower case letters. After the case of the string terms has been converted, the process continues in step 42 by replacing any abbreviations or alternate strings. As a general example, a physician or clinician may input a known abbreviation for a standard drug or frequency of administration. These abbreviations or alternate strings are replaced with a common text. The list of phrases and corresponding replacement text are located within database 14 (FIG. 5). In a preferred embodiment, a known input file available from Cerner Multum of Denver, Colo. is used to normalize against the standard abbreviations. The input file in the database 14 (FIG. 5) is extensible. This allows particular hospitals or other sites to add to the database those terms that are particular to the site.

After the abbreviations have been replaced in step 42, the process continues by determining whether a number exists at the end of a string, as shown in step 44. If the string ends with a number, the process continues at step 46 by determining whether separation of the numbers from the alpha string of the input string would result in only one letter remaining. If separation would result in an alpha string of more than one letter, the process continues at step 48 by separating the numbers from the alpha string. If, however, separation of the numbers from the alpha string would result in an alpha string of only one letter, the process will not separate the numbers and the alpha string, as shown at step 50. Separating numbers from alpha strings in step 44 allows a drug name and dosage without a space between the components (i.e. "ASA500") to be separated into search terms, for example. The determination step of step 46 prevents known medical abbreviations that use a combination alpha/numeric from being separated into separate search terms. For example, the known medical abbreviation "q3" will remain as a string rather than being separated into two separate search terms "q" and "3". If the string does not end in a number at step 44, or at the end of steps 48 and 50 if it does end in a number, the process continues by separating numbers that start a string as shown at step 52. This step allows the dosage amount to be separated from the dosage units. For example, if the input string was 650 m.g., the separation would result in two search terms, "650" and "m.g.". After starting numbers have been separated from the string, the process continues by determining whether periods and commas are present in the input string, as shown at step 54. Any commas that are present are removed from the string. If periods are present, the process continues by determining whether the period is placed before a number at step 56. If the period exists before a number, it is not removed, as shown at step 58. If, however, the period does not exist before a number, it is removed, as shown at step 60. This prevents a dosage or other value having a decimal indication from being erroneously converted. For example, if the input contained a string of "1.25", the system should not convert that to "125". If periods or commas are not present at step 54, following steps 58 and 60, the process continues at step 62 by determining whether any hyphens are present in the input string. If hyphens are present, the system then determines whether either of the hyphenated strings are less than four letters, as shown at step 64. If either of the hyphenated strings are less than four letters, as determined at step 64, the hyphens are eliminated, as shown at step 66. As an example, if the input string contained the alpha string "Z-pac", the hyphen would be eliminated and the search string will be changed to "Zpac". If, however, the strings that are hyphenated are four or more letters, the hyphen is eliminated and replaced with a space, as shown as step 68. As an example, if the input search string was "vibra-tabs", the process at step 68 would change it to "vibra tabs". This allows the system to give proper weight to search strings that are four or more letters while retaining the meaning of search terms that are three or less letters. If hyphens are not present in step 62, or following steps 66 and 68 if hyphens are present, the process continues by changing any slashes that have been input to spaces, as shown at step 70. This step accounts for an input of a combination drug order. For example, combination drugs are typically represented by an input "drug 1/drug 2/drug 3." Step 70 converts this string into three separate search terms, "drug 1", "drug 2", and "drug 3", resulting in better searching. The process continues by splitting the string into individual words, as shown at step 72. White space is used as the word "delimiter." After the string is split into individual words, in step 72, any needed antiflags are set in step 74. The antiflag is used when any search terms are present that change the sense of the search. Step 74 will then set a flag if any words, such as "free," are present, which reverse the sense of what is truly intended in the order. For example, if a search string incorporated "caffeine-free", the word "free" changes the sense of the search. In other words, it is clear that the order does not intend for drugs containing caffeine to be returned. Following step 74, the process continues at step 76 by removing any search terms that are numbers. The normalizing process of FIG. 2 is used to place the string in the best condition for broad searching. At this stage, any numbers that are present are assumed to be refinements and will be used at a later stage. The normalizing process continues at step 78 by removing words that are known to be common units, dosages, or routes. It is assumed that these are also refinements rather than key search terms. These common units are also contained within database 14 (FIG. 5).

As a general example, assume that the user of a remote computer 18 types in the order "Bayr-asa 650 m.g." For proper searching, the normalizer 20 (FIG. 5) will execute the steps of the process discussed above with respect to FIG. 2 to normalize the input string for better searching. In step 40, the process will convert all letters to lower case. Following step 40, the string will be changed to "bayr-asa 650 m.g." At step 42, any abbreviations and alternate strings are replaced. In this example, ASA is a known abbreviation for Aspirin. Thus, the process converts the string to "bayr-aspirin 650 m.g." In this example, the string terms do not end with a number, and the process will continue to step 52. In step 52, any numbers that start a string are separated. The search string thus becomes "bayr-aspirin 650 m.g." The process then continues at step 54 by determining whether periods and commas are present. In this example, periods are present, but do not exist before a number. Thus, the periods are removed at step 60. The resulting string becomes "bayr-aspirin 650 mg". The process then continues at step 62. In this instance, a hyphen is present, and the strings are both four or more letters. Thus, the hyphen is replaced with a space at step 68. The resulting string then becomes "bayr aspirin 650 mg". There are no multiple or combination drugs present in the string that contain slashes so that nothing is changed at step 70. At step 72, the string is split into individual words. In this example, the string is split into the individual words "bayr", "aspirin", "650", and "mg". Again, in this example, no words are present that would result in the setting of an antiflag. Thus, the process continues with step 76 where any numbers are removed. The resulting search terms are "bayr", "aspirin", and "mg". Finally, the normalizing process continues at step 78 by removing words that are known to be common units, dosages, or routes. Collectively, the common units, dosages and routes are known as "order parameters". In this example, the resulting search terms that remain are "bayr" and "aspirin". Step 78 thus removes the units "mg". At the end of the process of FIG. 2, the input string is normalized so that it can be used to search in a more meaningful manner. After the string has been normalized, the process continues by calculating the rough score as shown at step 34 in FIG. 1. The process of calculating a rough score of step 34 is more fully described with respect to FIG. 3.

Figures 3, 4:
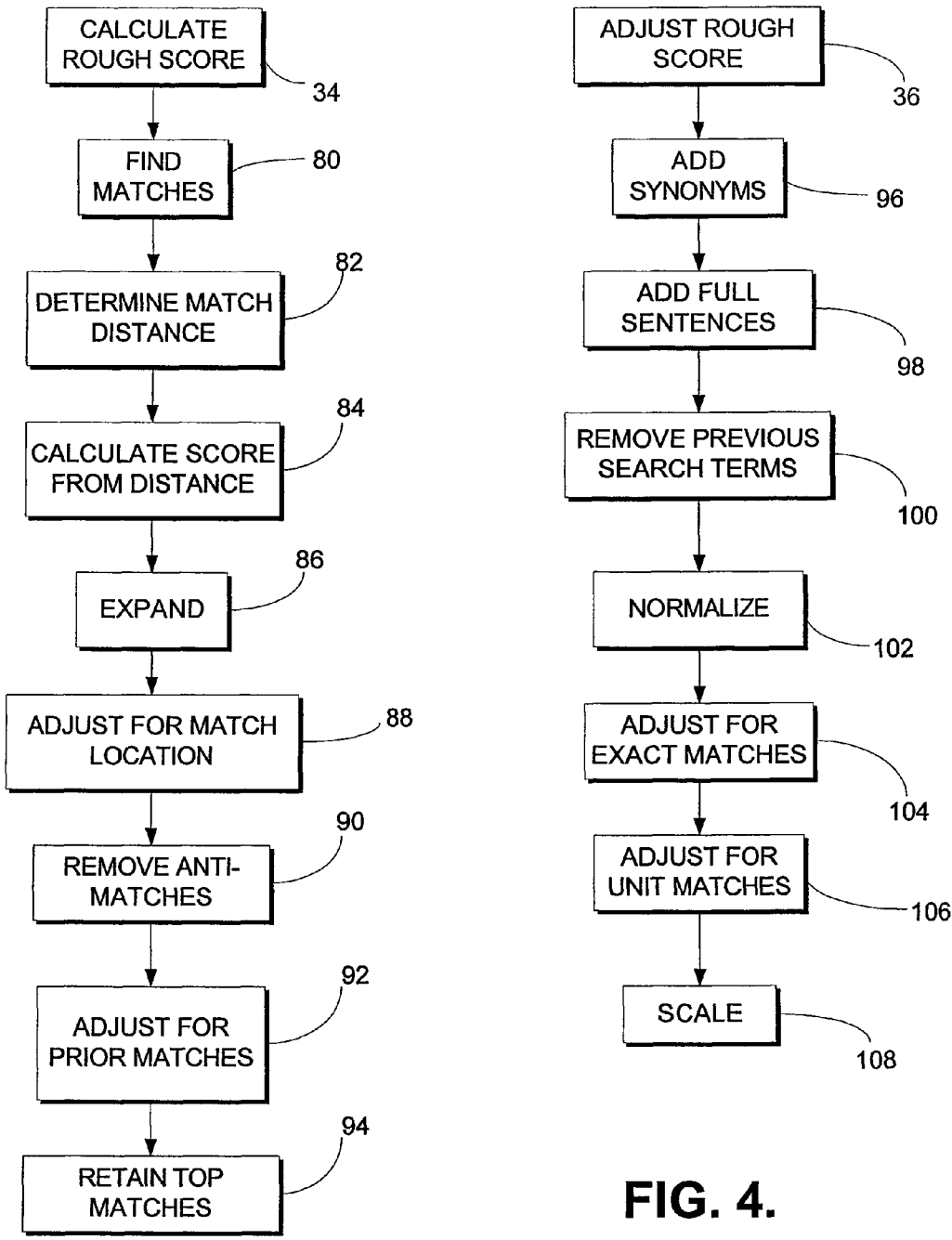
FIG. 3 is a flow diagram representing another component of the overall method of FIG. 1.
FIG. 4 is yet another flow diagram illustrating a different component of the overall process of FIG. 1.

As best seen in FIG. 3, the process of calculating a rough score begins by finding all matches in the database 14 (FIG. 5), as shown at step 80. The process shown in FIG. 3 is conducted for each term remaining after the normalizing step 32 (FIG. 1) with the results being combined during each pass. In finding the matches of step 80, a routine is used to return all matches within a specified distance. The distance is basically the number of changes (adding a letter, removing a letter, changing a letter) that need to be made to a search term to match a given string. Some of these matches may seem irrelevant, but the process later refines and eliminates the irrelevant terms. Thus, the routine that is used is given a specific search term and a list to be searched. The search term is one resulting from the normalizing step 32 (FIG. 1). The list to be searched is contained within database 14 (FIG. 5). In a preferred embodiment, the amatch ( ) routine provided by the String::approx library is used in step 80. The preferred specified distance is currently four (units), although it should be understood that other specified distances could also be used.

Specifying a distance of a lesser number will decrease the number of terms returned at step 80, while increasing the specified distance will increase the number of terms returned at step 80. For each match that is found at step 80, the process continues by determining the match distance, as shown at step 82. Thus, step 82 takes each match found at step 80 and calculates the distance of the match. In a preferred embodiment, the adist ( ) routine provided by the String::approx library is used to determine the distance of the match. Given the distance of the match determined at step 82, a score is calculated at step 84 from the distance. In this calculation, it is assumed that longer search terms are more important for matching. Thus, a long search string that is only distance 1 away from a match ends up ranking higher than a shorter search string that is distance 1 away. The formula used in step 84 is "score=1−distance/length(search string)". An exact match will have a distance of 1 resulting in a score of 100 percent. Following step 84, each score is expanded in step 86. The expansion step 86 converts the score into a larger value. The expansion is needed to allow further refinement based on other parameters. Again, the length of the search string is used to give more weight to matches with longer strings. This takes into account the fact that if a doctor took the time to enter a long string, it can be assumed that the string is an important search term. The calculation used to expand the score in step 86 is "Score=100×Score×Length(search string)." After the score has been expanded, it is adjusted for the match location, as shown in step 88. A routine is used to determine where the first match is made from a given search term. In a preferred embodiment, the aindex ( ) routine provided by the String::approx library is used to find the offset where the match first occurred. Continuing with step 88, if the match is at the beginning of the word, the score is increased. This accounts for the fact that matches at the beginning of a string are more likely to correspond to the intended order, as opposed to matches that are found later in the string. The calculation used to increase the score for matches at the beginning of a word is "score=score+(10×length (search string))+1. If the match is not at the beginning of a word, the score is reduced. The calculation used to reduce the score is "score=score−offset". The process then continues by removing all matches for which an antiflag has been set, where the matched item has a word in it that reverses the meaning of the match and the negative word is not the matched portion of the item. If this is the case, the search term is removed from the set. The process then continues at step 92 by adjusting for any prior matches. This then increases the score for a search string that contained a previous match. The calculation used to increase the score is "score=larger score+(smaller score/4)". The process of the rough score calculation concludes in step 94 by retaining the top matches. In a preferred embodiment, the top 100 matches are retained. It should be understood that more or less matches can be retained for further processing.

As an example of the rough score calculation, if the normalized string from the example above of "bayr aspirin" is used, two search terms "bayr" and "aspirin" are passed in. Given these search terms, the process of FIG. 3 proceeds as shown in Table 1 below. Table 1 shows a small representative sample of matches for illustrative purposes.

TABLE 1

| Calculate Rough Score | Pass 1, "bayr" | Pass 2, "aspirin" |
|---|---|---|
| Find Matches (80) | "maxair", "metaprel", "blocadren", "bayer aspirin", "cobal 1000" | "guanidine", "aspirlow", "aspergum original", "basiliximab", "litecoat aspirin" |
| Determine match distance (82) | Sampling of distance 1 matches: "bayer childrens aspirin", "carbatrol", "bayer aspirin", "baycol", "brethaire" | Sampling of distance 0 (exact) matches: "litecoat aspirin", "aspirin codeine", "aspirin", "bayer aspirin", "norwich aspirin" |
| Calculate score from distance (84): | 75%-bayer childrens aspirin 75%-carbatrol 75%-bayer aspirin 75%-baycol 75%-brethaire | 100%-litecoat aspirin 100%-aspirin codeine 100%-aspirin 100%-bayer aspirin 100%-norwich aspirin |
| Expand (86) | 300-bayer chilrens aspirin 300-carbatrol 300-bayer aspirin 300-baycol 300-brethaire | 700-litecoat aspirin 700-aspirin codeine 700-aspirin 700-bayer aspirin 700-norwich aspirin |
| Locate offset (88) | 0: bayer childrens aspirin 3: carbatrol 0: bayer aspirin 0: baycol 0: brethaire | 9: litecoat aspirin 0: aspirin codeine 0: aspirin 6: bayer aspirin 8: norwich aspirin |
| Adjust for match location (88) | 341: bayer childrens aspirin 297: carbatrol 341: bayer aspirin 341: baycol 341: brethaire | 771: litecoat aspirin 771: aspirin codeine 771: aspirin 771: bayer aspirin 771: norwich aspirin |
| Remove anti matches (90) | none removed | none removed |
| Adjust for prior matches (92) | 341: bayer childrens aspirin 297: carbatrol 341: bayer aspirin 341: baycol 341: brethaire | 771: litecoat aspirin 771: aspirin codeine 771: aspirin 856.25: bayer aspirin 771: norwich aspirin |
| Retain top matches (94) | 341: bayer childrens aspirin 297: carbatrol 341: bayer aspirin 341: baycol 341: brethaire | 771: litecoat aspirin 771: aspirin codeine 771: aspirin 856.25: bayer aspirin 771: norwich aspirin |

The matches are found using the amatch( ) routine in step 80, which returns, for example, "maxair" for the term "bayr". Maxair is a match due to the string "xair", which can be changed to "bayr" by substituting "b" for "x" and "y" for "i", or a distance 2 for two changes. In step 82, a sampling of distance 1 matches is shown. For example, "baycol" is a distance 1 match because the string "bayr" is found within "baycol" with only one change if an "r" is substituted for the "c".

The score from the distance is calculated at step 84. For a distance 1 match for the term "bayr" this calculation is score=1−(¼), or 75%. Note that for exact matches this score from the distance will always equal 100%. The score is then expanded in step 86. The formula is score=100*score*length (search string). For the term "bayr" this results in score=100*75%*4=300. After the score is expanded, the match is adjusted for the match location at step 88. The first part of this step is to locate the offset in the match. For the term "bayr" one distance 1 match is shown as "carbatrol." The offset for this match is 3, because the string "batr" begins at the third position in a zero-based counting system. Using that offset, the score is adjusted for the match location. For those matches with a match at the beginning of a word, the score becomes score=score+(10*length(search string))+1. So for the term "baycol" the score becomes score=300+(10*4)+1=341. For terms not matching at the beginning of a word, the score is adjusted to score=score−offset. For the term "carbatrol" the score becomes 300−3=297.

The process next removes any anti matches. In this example, no anti matches are present, so none are removed. The process continues at step 92 by adjusting for previous matches. Because the term "bayr" is the first term passed through the system, no adjustments will be made. As seen in the second column of Table 1, adjustments can be made in the second column for the term "aspirin". If a different word in the string is matched, the score is adjusted to score=larger score+(smaller score/4). For the string "bayer aspirin", the match occurred in both column 1 and column 2. The score is thus adjusted to score=771+(341/4)=856.25. After this calculation, the top matches are retained at step 94.

After the rough score for each of the search terms has been calculated, as set forth with respect to FIG. 3, the rough score is adjusted at step 36. This process is more fully explained with reference to FIG. 4. As best seen in FIG. 4, the process begins at step 96 by adding any synonyms to the previously found matches. Any synonyms are given the same score as their previously scored counterpart. This is illustrated in Table 2. These synonyms are also contained in the database 14 (FIG. 5). Again, the Multum database can be used for this purpose. After the synonyms have been added at step 96, the drug matches are expanded into the full sets of sentences containing that drug as shown at step 98. The drug sentence will typically contain the drug, a dosage and unit, the form of the drug, and its frequency. At step 100, any previously searched terms are eliminated. This prevents terms that have already been searched and scored in the process of step 34 from being further considered. Thereafter, the remaining sentences are normalized at step 102. The normalizing process of step 102 is the same as that described with respect to FIG. 2, with the exception that steps 76 and 78 regarding the removal of numbers and units are not performed.

The process continues at step 104 by adjusting for exact matches. At step 104, the distance of each term in the sentence is determined. Again, a routine is used that returns the number of changes that need to be made to a search term to match a given string. In a preferred embodiment, the adist ( ) routine provided by the String::approx library is used for this purpose. In performing this calculation, the equation "score=score+(3−ABS(distance))" is used. Following step 104, adjustments are made for unit matches, as shown in step 106. If the matched term is a number and it is an exact match (distance 0), the score will be increased. The calculation used to increase the score is "score=score+5". It is assumed that if the units match the search terms exactly, it is more likely that the sentence is an order intended by the entering health care professional. At steps 104 and 106, the goal is to make relatively small score adjustments that result in pushing the better matches to the top of the list. The adjustment should be small so that they do not overwhelm earlier search term scores. If the term is a number with a term after it that is a string, the score is again adjusted upwardly if the two together match as a whole. The upward adjustment reflects the significance of matching terms together in interpreting the entry. The calculation for this increase in score is "score=score+7". At this point, the top matches have been retained and scored. These scores have been refined. The scores are then scaled as shown in step 108. The scaling process ranks the top score as a score of 100 and adjusts the remaining scores correspondingly. The top matches are then displayed to the entering health care professional at the remote computer 18 (FIG. 5) for eventual selection of the order. The number of matches returned to computer 18 (FIG. 5) can be limited to those that are most likely to reflect the intended order of the physician.

As an example of the rough score adjustment of the rough scores calculated as an example with respect to Table 1, the process of FIG. 4 proceeds as shown in Table 2 below.

TABLE 2

| Adjust rough score (36) | Result |
|---|---|
| Add synonyms (96) | 856.25: bayer aspirin |
| | 856.25: aspirin diphenhydramine |
| | 856.25: bayer childrens aspirin |
| | 856.25: bayer aspirin pm extra strength |
| | 771: halfprin |
| Add full sentences (98) | 856.25: ASPIRIN 300 mg tab PO Q4H |
| | 856.25: ASPIRIN 975 mg ec tab PO QID |
| | 856.25: ASPIRIN 1300 mg tab PO Q4H |
| | 856.25: ASPIRIN 650 mg supp PR Q4H |
| | 856.25: ASPIRIN tab 2 tab PO QD |
| Remove previous search terms (100) | 856.25: [aspirin] 300 mg tab PO Q4H |
| | 856.25: [aspirin] 975 mg ec tab PO QID |
| | 856.25: [aspirin] 1300 mg tab PO Q4H |
| | 856.25: [aspirin] 650 mg supp PR Q4H |
| | 856.25: [aspirin] tab 2 tab PO QD |
| Normalize (102) | 856.25: [aspirin] 300 mg tab po q4h |
| | 856.25: [aspirin] 975 mg ec tab po qid |
| | 856.25: [aspirin] 1300 mg tab po q4h |
| | 856.25: [aspirin] 650 mg supp pr q4h |
| | 856.25: [aspirin] tab 2 tab po qd |
| Determine match distance (104) | 860.25: [aspirin] 300 mg tab po q4h |
| | 860.25: [aspirin] 975 mg ec tab po qid |
| | 860.25: [aspirin] 1300 mg tab po q4h |
| | 862.25: [aspirin] 650 mg supp pr q4h |
| | 856.25: [aspirin] tab 2 tab po qd |
| Adjust for exact matches (104) | 860.25: [aspirin] 300 mg tab po q4h |
| | 860.25: [aspirin] 975 mg ec tab po qid |
| | 860.25: [aspirin] 1300 mg tab po q4h |
| | 867.25: [aspirin] 650 mg supp pr q4h |
| | 856.25: [aspirin] tab 2 tab po qd |
| Adjust for unit matches (106) | 860.25: [aspirin] 300 mg tab po q4h |
| | 860.25: [aspirin] 975 mg ec tab po qid |
| | 860.25: [aspirin] 1300 mg tab po q4h |
| | 874.25: [aspirin] 650 mg supp pr q4h |
| | 856.25: [aspirin] tab 2 tab po qd |
| Scale (108) | 100: Bayer aspirin 650 mg supp PR Q4H |
| | 98.399: aspirin 300 mg tab PO Q4H |
| | 98.399: aspirin 975 mg ec tab PO QID |
| | 98.399: aspirin 1300 mg tab PO Q4H |
| | 97.941: aspirin tab 2 tab PO QD |

It should be noted that the results shown in the second column do not match one-to-one with the results shown in Table 1. The results shown in Table 2 are merely a sample of exemplary results for the given step. The scores in the second column begin with most of the results listed coming from the previous match "bayer aspirin". This result has a score of 856.25 in the example. The process begins by adding in drug synonyms in step 96. To this point in the process, the process is directed to matching specific drugs to the input string. In steps 98-108, the input string is used to search against full order sentences to identify the best matches of entire order sentences. Specifically, the matches are expanded into full sentences in step 98. Any previously searched terms, such as aspirin, are removed in step 100. The results are then normalized in step 102, as described above with reference to FIG. 2.

The process continues at step 104 by adjusting for exact matches. The first part of this step is to determine the match distance. For the search example in Table 2, the search terms are "650" and "mg". The score is adjusted at step 104 based upon the match distance. For example, the sentence "[aspirin] 300 mg tab po q4h" has a score of 856.25 that is adjusted to score=score+(3−abs(distance)) or score=856.25+(3−2)+(3−0)=860.25, because "300" has a distance of 2 from "650" and "mg" is an exact match. The sentence "[aspirin] 650 mg supp pr q4h" becomes score=856.25+(3−0)+(3−0)=862.25.

If the matched term is a number and it is an exact match, the process adds to the score at step 104. Thus, in this example, "[aspirin] 650 mg supp pr q4h" becomes score=862.25+5=867.25. The process continues with step 106 by adjusting for unit matches. If the term is a number with a term after it that is a string, the score is boosted by seven so that "[aspirin] 650 mg supp pr q4h" becomes score=867.25+7=874.25. The remaining scores are then scaled such that the top score is 100 with the remainder adjusted accordingly.

It can therefore be seen that the process of the present invention allows an individual to type in a limited set of order information at a remote computer 18 (FIG. 5). The invention processes that limited information and returns to the user a number of full sentence orders that most likely correspond to the order intended by the doctor or the health care professional. The process can be executed quickly so that results are returned to the user of remote computer 18 (FIG. 5) in a timely fashion. Moreover, the standard abbreviations that the doctor is accustomed to using are incorporated in the database 14 (FIG. 5) and can continue to be used by the doctor.

Although the invention has been described with reference to the preferred embodiment illustrated in the attached drawing figures, it is noted that substitutions may be made and equivalents employed herein without departing from the scope of the invention as recited in the claims. For example, additional steps may be added and steps omitted without departing from the scope of the invention.

What the invention claims is:

1. A computer-implemented method for normalizing an input string indicative of a health care order, the normalizing to facilitate searching for possible intended health care order sentences, comprising:

receiving, utilizing a first computer process, the input string indicative of a desired healthcare order having terms therein;

normalizing, utilizing a second computer process, the terms of the healthcare order, wherein the normalizing includes:

replacing any abbreviations with known terms corresponding to the respective abbreviations;

determining whether any of the terms end in a number string;

based on a determination that a term ends in a number string, determining if only one letter is present before the number;

based on a determination that only one letter is present before the number, maintaining the letter-number string; and based on a determination that more than one letter is present before the number, separating the letter string from the number string;

wherein the first and second computer processes are executed utilizing one or more computing devices.

2. The computer-implemented method of claim 1, further comprising separating any number string at the beginning of any term.

3. The computer-implemented method of claim 2, further comprising removing any periods present in terms that are not located before a number.

4. The computer-implemented method of claim 3, further comprising removing any hyphens present in any term if the term is less than four characters long.

5. The computer-implemented method of claim 4, further comprising setting an anti-flag for any found, pre-determined anti-terms.

6. The computer-implemented method of claim 5, further comprising removing any terms containing only numbers.

* * * * *